United States Patent [19]

Weinberger et al.

[11] Patent Number: 5,549,884
[45] Date of Patent: Aug. 27, 1996

[54] RAT OR MOUSE EXHIBITING BEHAVIORS ASSOCIATED WITH HUMAN SCHIZOPHRENIA

[75] Inventors: Daniel R. Weinberger, Washington, D.C.; Barbara K. Lipska, Annandale, Va.; George E. Jaskiw, Lyndhurst, Ohio

[73] Assignee: The United States of America as represented by the Secretary of the Department of Health and Human Services, Washington, D.C.

[21] Appl. No.: 967,367

[22] Filed: Oct. 28, 1992

[51] Int. Cl.$^6$ .................... A61K 49/00; C12N 15/00; G01N 37/00
[52] U.S. Cl. .................. 424/9.2; 424/9.1; 800/2; 935/111
[58] Field of Search .................. 424/9, 9.1, 9.2; 800/2

[56] References Cited

PUBLICATIONS

R. L. Port et al. (1991) Brain Research Bulletin 26:993–996.
B. K. Lipska et al. (1992) Brain Research 585:1–6.
J. Feldon et al. (1992) J. Psychiatric Research 26(4):345–366.
A. B. Scheibel et al. (1993) 19(1):21–33.
L. E. Adler et al. (1991) Schizophrenia Bulletin 17(1):19–24.
Beauregard, M., et al., "Schizophrenia a Result of Early Damage to the Hippocampal Formation? A Behavioral Study in Primates," *Society for Neuroscience Abstracts*, vol. 18(2), p. 872 (1992).
Lipska, B. K., et al., "Postbubertal Emergence of Mesolimbic Dopaminergic Supersensitivity after Excitotoxic Lesions of Ventral Hippocampus in the Rat," *Society for Neuroscience Abstracts*, vol. 18(2), No. 472.1 (1992).

*Primary Examiner*—Jacqueline M. Stone
*Assistant Examiner*—Johnny F. Railey, II
*Attorney, Agent, or Firm*—Townsend and Townsend and Crew LLP

[57] ABSTRACT

This invention provides a unique and surprisingly accurate animal model for human schizophrenia. The animals are brain damaged while prepubescent. The brain damage consists of a ventral hippocampus lesion induced by exposure of the hippocampus region to a neurotoxin. When the animal reaches puberty, abnormal behavior and a number of biological phenomena associated with schizophrenic symptoms emerge. These animals are useful for assaying pharmaceutical compounds for anti-schizophrenic activity.

11 Claims, 5 Drawing Sheets

RAT OR MOUSE EXHIBITING BEHAVIORS ASSOCIATED WITH HUMAN SCHIZOPHRENIA

BACKGROUND OF THE INVENTION

This invention provides a unique and surprisingly accurate animal model for human schizophrenia. The animals are brain damaged while prepubescent. The brain damage consists of a ventral hippocampus lesion induced by exposure of the hippocampus region to a neurotoxin. When the animal reaches puberty, abnormal behavior and a number of other biological phenomena associated with schizophrenic symptoms emerge. These animals are useful for assaying pharmaceutical compounds for anti-schizophrenic activity.

SUMMARY OF THE INVENTION

The present invention provides methods of assaying the anti-schizophrenic potential of pharmaceutical compositions. The methods comprise the following steps: (a) inducing or creating a lesion in the ventral hippocampus of a prepubescent mammal, i.e., a mammal which has not yet reached puberty, using a neurotoxin so that the lesion is able to induce abnormal behavior in postpubescent mammals; (b) nurturing or raising the mammal until postpuberty, i.e., until the mammal reaches sexual maturity; (c) administering to the mammal a pharmaceutical composition thought to have anti-schizophrenic properties; and (d) determining the mammal's response to the pharmaceutical composition. The anti-schizophrenic potential of the pharmaceutical composition is assessed by objectively measuring the mammal's behavior following administration of the pharmaceutical composition. The mammal's behavior is measured or monitored using standard tests well-known by those skilled in the art. The behaviors which are measured typically include the following: locomotor activity in a cage, in unfamiliar or novel environments, after injection or administration of drugs (e.g., amphetamines), after mild electric shock, after exposure to sensory stimuli (e.g., noise), in water (swim test), after immobilization, in social interactions, and in various learning and reward paradigms.

The present invention also provides methods of assaying the anti-excessive limbic dopamine activity potential of pharmaceutical compositions. The methods comprise the following steps: (a) inducing a lesion in the ventral hippocampus of a prepubescent mammal using a neurotoxin so that the lesion is able to induce excessive limbic dopamine activity in postpubescent mammals; (b) nurturing or raising the mammal until postpuberty; (c) administering a pharmaceutical composition thought to have anti-excessive limbic dopamine activity; and (d) determining the mammal's response to the pharmaceutical composition. The anti-excessive limbic dopamine activity potential of the pharmaceutical composition is assessed by objectively measuring the mammal's behavior following administration of the pharmaceutical composition. The mammal's behavior is measured or monitored using standard tests well-known by those skilled in the art.

The present invention further provides mammals which are artificially brain damaged through a lesion in the ventral hippocampus. The lesion is created or induced through the use of a neurotoxin when the mammal is prepubescent, and the lesion is capable of inducing abnormal behavior in the postpubescent mammal. The mammals of the present invention can be used, for example, to assay the anti-schizophrenic potential of pharmaceutical compositions. Additionally, the mammals of the present invention can be used to assay the anti-excessive limbic dopamine activity potential of pharmaceutical compositions.

DEFINITIONS

Figure 1:
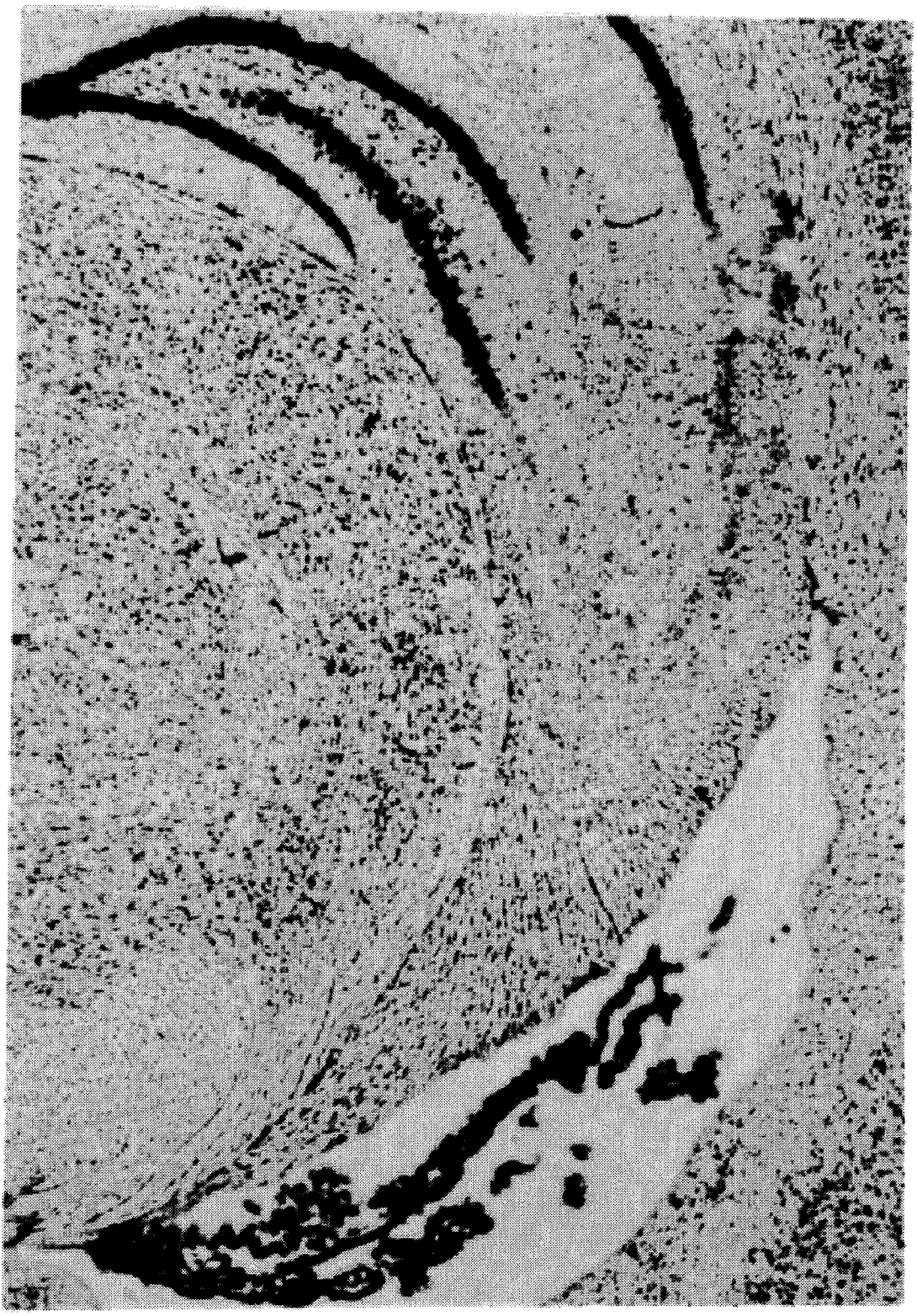
FIG. 1 shows a Nissl-stained coronal section (approximately 5.0 mm posterior from the bregma) through the rat brain with neonatal ibotenic acid lesion of the ventral hippocampal formation. The rat was sacrificed 2 months after the lesion. Arrows point to areas of focal neuronal loss (CA3-4) with secondary microglial and astrocytic proliferation in the left hippocampus. The lesion extends further posterior (i.e., ventrally). Bar=1 mm.

The word "abnormal behavior" is used herein to refer to behavior which statistically differs from sham mammals which are similarly treated except for the application of the neurotoxin. Abnormal behavior consists of any number of standard behaviors which can be objectively measured and statistically compared. These behaviors include, but are not limited to, ataxia, rapid limb movement, eye movement, breathing, motor activity, cognition, emotional behaviors and social behaviors. The abnormal behaviors which are preferably studied are those which emerge after puberty and which are schizophrenic-like. Such behaviors include, but are not limited to, stress-induced hyperactivity, dopamimetic hypersensitivity, abnormal social interaction, impaired learning, and abnormal reward behavior.

The phrase "neurotoxin" is used herein to refer to a substance which is poisonous or destructive to nerve tissue such as, for example, an excitotoxin. Excitotoxins specifically kill neurons by over-excitation. Generally, such toxins affect the glutamate receptors located on the neurons.

The phrase "prepubescent mammal" is used herein to refer to a mammal which is not sexually mature, i.e., a mammal which has not yet reached puberty.

The phrase "ventral hippocampus" is used herein to refer to that portion of the hippocampus which is near the underside of the brain.

The phrase "ventral hippocampus lesion" is used herein to refer to the destruction, removal or alteration of a portion of the ventral hippocampus either unilaterally or bilaterally such that abnormal behavior results in the postpubescent mammals.

DETAILED DESCRIPTION

The present invention provides a unique animal model of schizophrenia for testing and developing new treatments for this illness and other related psychotic illnesses (e.g., manic-depression). The animal model is based upon inducing a specific brain lesion in the ventral hippocampus of mammals. The model accounts for phenomena associated with schizophrenia in humans, such as, for example, structural abnormalities of temporal limbic system, functional deficits in prefrontal cortex, hyperresponsiveness of the dopaminergic mesolimbic system, hypersensitivity to stress, and delayed postpubertal emergence of the hypersensitivity. This high fidelity rat model of the pathophysiological mechanisms implicated in schizophrenia is invaluable in developing new therapies (e.g., drug, behavioral, etc.) based on primary, rather than on secondary manifestations of the disease.

The ventral hippocampal lesions are induced in prepubescent mammals, i.e., mammals which have not yet reached puberty. Such mammals include any of the typical laboratory animals such as, for example, rats, mice, guinea pigs, dogs, monkeys and the like. Neonatal individuals are preferred because recent theories of schizophrenia point to brain damage in early development. Prior to creating the ventral hippocampal lesions, the animals are anesthetized by any number of known procedures, taking care that the anesthesia does not interfere with the neurotoxin's ability to lethally affect the glutamate receptors of the target neurons. The presently preferred anesthesia of the invention is hypothermia, i.e., placing the animal on wet ice.

Once the mammal is anesthetized, it is immobilized and placed into a stereotaxic device (e.g., Kopf stereotaxic instrument, Stolting stereotaxic apparatus, or others). Such devices are commercially available and allow for precise location of specific lesion sites based on various reference points on the exterior of the animal's body. Brain atlases are available for most mammals and are used to locate the precise point of the ventral hippocampus. An example of inducing a ventral hippocampus lesion in a rat is set forth in the examples provided below.

In general, the animal is anesthetized, placed in the stereotaxic apparatus, and a small incision is made in the scalp of the animal. Once the incision is made, a hypodermic needle is inserted into the ventral hippocampus and a standard laboratory microsyringe pump is used to infuse the neurotoxin. The neurotoxin used can be selected from a number of known agents which lethally affect neurons usually, but not exclusively, by over-exciting their glummate receptors. Examples of such neurotoxins include, but are not limited to, ibotenic acid, N-methyl-D-aspartic acid, kainic acid, dihydrokainate, DL-homocysteate, L-cysteate, L-aspartate, L-glutamate, colchicine, ferric chloride, omega-conotoxin GVIA, 6-hydroxy-dopamine. Certain neurotoxins are preferred, namely those which are excitotoxins. Preferred excitotoxins include, but are not limited to, ibotenic acid, N-methyl-D-aspartic acid, and kainic acid. In the presently preferred embodiment of the invention, ibotenic acid is the excitotoxin used.

The toxins are applied by mixing them with a physiologically compatible vehicle or solution such as, for example, saline solutions, artificial cerebrospinal fluid, or cerebrospinal fluid from the animal itself. The toxins are infused using an infusion pump through a hypodermic needle inserted into the mid-region of the ventral hippocampus. The amount of the toxin will vary depending upon the animal and the particular neurotoxic compound used, but, in general, one would want to use a neurotoxin concentration which provides a 100% kill of the appropriate hippocampal neurons while not injuring other tissue and sites. The lesion is considered to be properly induced when a postmortem of the mammal reveals that the target region is devoid of neurons.

Once the lesion has been made, the prepubescent mammals are allowed to grow to sexual maturity. The postpubescent mammals are then assessed for abnormal behaviors. Such behaviors are well known for a host of common mammals and typically include the following: locomotor activity in a cage, in unfamiliar or novel environments, after injection or administration of drugs (e.g., amphetamines), after mild electric shock, after exposure to sensory stimuli (e.g., noise), in water (swim test) and after immobilization, in social interactions, and in various learning and reward paradigms. Abnormal behaviors in rats have been routinely analyzed using standard tests well-known by those skilled in the art, some of these behavioral tests are explained, in brief, below:

The swim test generally involves immersion of the rat in water for a set period of time and subsequent analysis of locomotor activity, e.g., distance traveled. Locomotor activity is objectively measured by direct observation and/or through the use of automatic photocell monitor. The locomotor activity, e.g., distance traveled, is statistically analyzed using standard statistical tests. (See, e.g., G. E. Jaskiw, et al., *Pharm. Bioch. Behav.* 41:607–609 (1992)).

The isolation test comprises housing the rats in cages without any sensory contact and abnormal behaviors are measured in terms of activity (e.g., distance traveled), learning (e.g., number of correct responses when placed in a maze), emotionality (e.g., aggressiveness), response to dopamimetics, etc. The various behaviors measured are statistically analyzed using standard statistical tests. (See, e.g., G. Blanc, et al., *Nature* 284:265–267 (1980)).

The social interaction test involves exposing the rat to other animals in a variety of settings, objectively measuring subsequent social behaviors such as, for example, touching, climbing, sniffing and mating, and statistically analyzing the behaviors measured. (See, e.g., S. E. File, et al., *Pharmacol. Bioch. Behav.* 22:941–944 (1985); R. R. Holson, *Phys. Behav.* 37:239–247 (1986)).

The prepulse inhibition of startle response test involves exposing the animal to a sensory stimulus, objectively measuring the startle responses of the animal to similar acoustic or tactile stimuli, and statistically analyzing the behaviors measured. (See, e.g., M. A. Geyer, et al., *Brain Res. Bull.* 25:485–498 (1990)).

The electric shock test generally involves exposure to an electrified surface and measurement of subsequent behaviors such as, for example, motor activity, learning, social behaviors. The behaviors measured are statistically analyzed using standard statistical tests. (See, e.g., G. J. Kant, et al., *Pharm. Bioch. Behav.* 20:793–797 (1984); N. J. Leidenheimer, et al., *Pharmacol. Bioch. Behav.* 30:351–355 (1988)).

The tail-pinch or immobilization test involves applying pressure to the tail of the animal and/or restraining the animal's movements, subsequently measuring, for example, motor activity, social behavior, and cognitive behavior, and statistically analyzing the behaviors measured. (See, e.g., M. Bertolucci D'Angic, et al., *Neurochem.* 55:1208–1214 (1990)).

The novelty test generally comprises exposure to a novel environment and/or novel objects, measuring, for example, the animal's motor behavior in the novel environment and/or around the novel object, and statistically analyzing the behaviors measured. (See, e.g., D. K. Reinstein, et al., *Pharm. Bioch. Behav.* 17:193–202 (1982); B. Poucet, *Behav. Neurosci.* 103:1009–10016 (1989); R. R. Holson, et al., *Phys. Behav.* 37:231–238 (1986)).

The learned helplessness test involves exposure to stresses, e.g., noxious stimuli, which cannot be affected by the animal's behavior and subsequently exposing the animal to a number of behavioral paradigms. The animal's behavior is statistically analyzed using standard statistical tests. (See, e.g., A. Leshner, et al., *Behav. Neural Biol.* 26:497–501 (1979)).

The Morris water-maze test comprises learning spatial orientations in water and subsequently measuring the animal's behaviors, such as, for example, by counting the number of incorrect choices. The behaviors measured are statistically analyzed using standard statistical tests. (See, e.g., E. M. Spruijt, et al., *Brain Res.* 527:192–197 (1990)).

The passive avoidance or shuttle box test generally involves exposure to two or more environments, one of which is noxious, and a choice must be learned. Behavioral measures include, for example, response latency, number of correct responses, and consistency of response. (See, e.g., R. Ader, et al., *Psychon. Sci.* 26:125–128 (1972); R. R. Holson, *Phys. Behav.* 37:221–230 (1986)).

The food avoidance test involves exposure to novel food and objectively measuring, for example, food intake and intake latency. The behaviors measured are statistically analyzed using standard statistical tests. (See, e.g., B. A. Campbell, et al., *J. Comp. Physiol. Psychol.* 67:15–22 (1969)).

The elevated plus-maze test comprises exposure to a maze, without sides, on a platform, the animal's behavior is objectively measured by counting the number of maze entries and maze learning, and the behavior is statistically analyzed using standard statistical tests. (See, e.g., H. A. Baldwin, et al., *Brain Res. Bull.*, 20:603–606 (1988)).

The stimulant-induced hyperactivity test involves injection of stimulant drugs (e.g., amphetamines, cocaine, PCP, etc. ), and objectively measuring, for example, motor activity, social interactions, cognitive behavior. The animal's behaviors are statistically analyzed using standard statistical tests. (See, e.g., P. B. S. Clarke, et al., *Psychopharmacology* 96:511–520 (1988); P. Kuczenski, et al., *J. Neuroscience* 11:2703–2712 (1991)).

The dopamine agonists-induced stereotypy test involves injection of dopamine agonists, e.g., apomorphine, quinpirole, etc., and objectively measuring frequency and pattern of certain motor behaviors such as, for example, sniffing, licking, biting, etc. Subsequently, the behaviors measured are statistically analyzed using standard statistical tests. (See, e.g., B. Scatton, et al., *Brain Res.* 232:331–343 (1982)).

The self-stimulation test generally comprises providing the rat with the opportunity to regulate electrical and/or chemical stimuli to its own brain. Behavior is measured by frequency and pattern of self-stimulation. Such behaviors are statistically analyzed using standard statistical tests. (See, e.g., S. Nassif, et al., *Brain Res.*, 332:247–257 (1985); W. L. Isaac, et al., *Behav. Neurosci.* 103:345–355 (1989)).

The reward test involves shaping a variety of behaviors, e.g., motor, cognitive, and social, measuring, for example, rapidity and reliability of behavioral change, and statistically analyzing the behaviors measured. (See, e.g., L. E. Jarrard, et al., *Exp. Brain Res.* 61:519–530 (1986)).

The DRL (differential reinforcement to low rates of responding) performance test involves exposure to intermittent reward paradigms and measuring the number of proper responses, e.g., lever pressing. Such behavior is statistically analyzed using standard statistical tests. (See, e.g., J. D. Sinden, et al., *Behav. Neurosci.* 100:320–329 (1986); V. Nalwa, et al., *Behav Brain Res.* 17:73–76 (1985); and A. J. Nonneman, et al., *J. Comp. Physiol. Psych.* 95:588–602 (1981).

The spatial learning test involves exposure to a complex novel environment, measuring the rapidity and extent of spatial learning, and statistically analyzing the behaviors measured. (See, e.g., N. Pitsikas, et al., *Pharm. Bioch. Behav.* 38:931–934 (1991); B. poucet, et al., *Brain Res.* 37:269–280 (1990); D. Christie, et al., *Brain Res.* 37:263–268 (1990); and F. Van Haaren, et al., *Behav. Neurosci.* 102:481–488 (1988)).

The visual, somatosensory and auditory neglect tests generally comprises exposure to a sensory stimulus, objectively measuring, for example, orientating responses, and statistically analyzing the behaviors measured. (See, e.g., J. M. Vargo, et al., *Exp. Neurol.* 102:199–209 (1988)).

The consummatory behavior test generally comprises feeding and drinking and objectively measuring quantity of consumption. The behavior measured is statistically analyzed using standard statistical tests. (See, e.g., P. J. Fletcher, et al., *Psychopharmacol.* 102:301–308 (1990); M. G. Corda, et al., *Proc. Nat'l Acad. Sci.* (USA) 80:2072–2076 (1983)).

All of the aforementioned references are incorporated herein by reference.

A statistical analysis of the various behaviors measured can be carried out using any conventional statistical program routinely used by those skilled in the art (such as, for example, ANOVA). A P value less than 0.05, i.e., $P<0.05$, is considered to be statistically significant. To statistically analyze abnormal behavior, a comparison is made between the behavior of a lesioned mammal and the behavior of a sham mammal. Sham mammals are similarly treated as those with the ventral hippocampus lesion (i.e., lesioned mammals), except that their hippocampi have been treated with a harmless perfusate instead of an neurotoxin. Preferred behaviors are those which first become abnormal after puberty in lesioned animals and which mimic symptoms associated with humans afflicted with schizophrenia. Such behaviors include, but are not limited to, the following: stress-induced hyperactivity, dopamimetic hypersensitivity, abnormal learning and reward behaviors, and social interactions. Tests used to measure these schizophrenic-like behaviors include, but are not limited to, those mentioned above. For example, one could measure locomotor activity in a rat after exposure to a new environment, administration of a drug, or the swim test. By measuring, for example, the distance the lesioned animal traveled and comparing this distance to the distance the sham animal traveled, one can readily identify and analyze the abnormal behavior.

Once the lesion is present and reproducible abnormal behavior is established and understood, the mammals can subsequently be used to survey chemical compounds for anti-schizophrenic activity. The potential anti-schizophrenic drugs are administered in various amounts and the effect upon the abnormal behavior is monitored. The method of administration depends upon the drug being tested and can include oral, parenteral, transdermal or rectal administration. An effective drug is one which will reduce abnormal behavior to a degree that approaches the behavior of the sham mammal. For example, one could use a drug (such as, for example, haloperidol, clozapine, or other currently available antipsychotic drugs) and measure the drug's effect on locomotor activity or any other behavior described herein. If the abnormal behavior of the animal is found to decrease, i.e., be reduced, the drug is effective.

Additionally, the anti-excessive limbic dopamine activity potential of pharmaceutical compositions can be assessed by objectively measuring the dopamine activity of the mesolimbic system. The animal is sacrificed and the brain regions (medial prefrontal cortex, anteromedial corpus striatum and NAS) are dissected and frozen until analysis. The brain tissue is analyzed using standard methods of combined gas chromatography/mass fragmentography. Tissue samples are prepared for injection into the gas chromatography/mass fragmentography instruments using standard procedures known by those skilled in the art. These methods provide a chromatographic and quantitative analysis of the concentration of dopamine and its metabolites. Moreover, one can measure the anti-excessive limbic dopamine activity potential of a pharmaceutical drug by looking at the behaviors previously described because, for example, both novelty and amphetamine induced locomotion have been linked to mesolimbic DA transmission. If the abnormal behavior of the animal is found to decrease, i.e., be reduced, the drug is said to be an effective drug.

The invention will be described in greater detail by way of specific examples. The following examples are offered for illustrative purposes, and are intended neither to limit or define the invention in any manner. Those of skill will readily recognize that the examples can be varied in numerous, non-critical ways.

EXAMPLES

A. Surgery: Inducing A Ventral Hippocampus Lesion In A Rat

Pregnant Sprague-Dawley rats obtained at 14 days gestation (Zivic Miller Labs) were housed individually in breeding cages with a 12:12 h light-dark cycle and fed ad libitum, i.e., with free access to food and water. Litters of 4–8 male pups were formed. On postnatal day 7 (PD-7) (weight 15–18 g), pups within each litter were randomized to SHAM or LESION status and anesthetized by hypothermia (i.e., the rats were placed on wet ice for 10–20 min). An incision was made in the skin overlying the skull, and the rats were placed on the platform attached to a Kopf stereotaxic instrument. After immobilization of the rat by taping to the platform, 0.3 µl of ibotenic acid (Sigma Chemical Co., 10 µg/µl dissolved in an artificial cerebrospinal fluid, pH 7.4) for LESION animals or artificial cerebrospinal fluid for SHAM animals was infused using an infusion pump (Harvard Apparatus) bilaterally (i.e., two injections on each side) through a Hamilton needle into the ventral hippocampal formation at a flow rate of 0.15 µl/min at the stereotaxic coordinates: anterior-posterior (AP) −3.0 mm, medial-lateral (ML) ±3.5 mm, ventral-dorsal (VD) −5.0 mm, relative to bregma. The Hamilton needle was withdrawn 4 min after completion of the infusion.

After the operation, the pups were placed under a warming lamp, and then returned to their mothers. On PD-25, animals were weaned, separated by lesion status (i.e., ibotenic acid lesioned (LESION) or sham-operated (SHAM)) and grouped 2–3 to a cage. A total of four cohorts (N=20–28/cohort) of neonatally lesioned rats were utilized in the following experiments. In addition, a cohort of animals lesioned as adults (i.e., on PD-42) was prepared as previously described (Lipska, et al., Brain Res. 585:1–6 (1992)) for selected comparisons with neonatally lesioned rats.

B. Behavioral Testing: Assaying For Schizophrenic-Like Symptoms

The motor activity of two different cohorts of rats (N=9 and 14 SHAM, N=11 and 14 LESION within each cohort) was assessed at both 4 weeks (PD-35) and 7 weeks (PD-56) postoperatively in the following three testing conditions: (1) after exposure to a novel environment; (2) after saline injections; and (3) after amphetamine injections. For these tests, unacclimatized rats were moved to the monitor area at 9:00 AM and immediately placed in clear plexiglass photocell activity monitors (42×42×30 cm) (Omnitech model RXYZCM 16). Spontaneous locomotor activity was measured during a 60 min habituation period. Each rat then received a saline injection (1 mL/Kg, i.p.) and was returned to the photocell monitor for an additional 60 min period. At that point, 1.5 mg/kg of D-amphetamine (Sigma Chemical Co.) was administered intraperitoneal (i.p.) and locomotor activity was recorded for a final 90 min.

One of these cohorts was additionally exposed to a swim test 2 weeks after the last testing (i.e., on PD-70) to further explore the effects of stress in neonatally lesioned rats. For this test, rats were randomly assigned to four groups (i.e., SHAM/NO STRESS, SHAM/SWIM, LESION/NO STRESS, LESION/SWIM, N=8/ group) and after acclimatization to the testing area, they were placed for 15 min in cylindrical plexiglass containers covered with opaque paper (height and diameter 30 cm). The containers were filled either with sawdust (2 cm) (NO STRESS) or with water at room temperature (depth 23 cm) (SWIM). At the end of 15 min, all animals were transferred to dry cages with new bedding, and after 5 min, they were placed in photocell monitors. Locomotor activity was recorded for 95 min.

In a separate experiment, an additional group of rats was lesioned on PD-42 as previously described (Lipska, et al., Brain Res. 585:1–6 (1992)) and exposed to a swim test (on PD-70) to compare the response to stress with a neonatally lesioned group. The lesion was induced as follows. After induction of anesthesia with Equithesin 3 mL/Kg (i.p.), adult Sprague-Dawley rats (weight 220–240 g) were placed in a Kopf stereotaxic instrument. Ibotenic acid (6/µg/0.6 µl over 3 min) or an equal volume of vehicle was administered by infusion pump (Harvard Apparatus) bilaterally (2 injections on each side) through 26-gauge cannulae at the stereotaxic coordinates: AP −4.4 mm, ML 5.0 mm, VD −8.0 and −6.0 mm, with respect to bregma. Four weeks postoperatively (PD-70), animals were randomly assigned to four groups SHAM/NO STRESS, SHAM/SWIM, LESION/NO STRESS, LESION/SWIM (N=10/group), and exposed to a swim test, as previously described. After completion of the swim test, locomotor activity was recorded for 95 min.

Another neonatally lesioned testing-naive cohort (N=10 SHAM, N=17 LESION) was tested only once at PD-56 to control for the possibility that pre-exposure to D-amphetamine could affect the response on PD-56.

Another group of rats lesioned at PD-7 was treated for 3 weeks (i.e., from PD-35 until PD-56) with either vehicle or haloperidol to assess the effect of neuroleptic treatment on hyperlocomotion. The duration of treatment was chosen to approximate the subchronic duration of haloperidol administration associated with clinical response in patients with schizophrenia (Pickar, et al., *Schizophr. Bull.* 14:255–268 (1988)). At PD-35, neonatally operated rats were randomly assigned to four groups: SHAM/VEH, LESION/VEH, SHAM/HAL, LESION/HAL, N=7/group. The first two groups were treated once daily with vehicle (VEH, water with a drop of Tween 80®, an emulsifier and dispersing agent, adjusted to pH 5.6) given i.p. for 3 weeks, while the other two groups were injected with haloperidol (HAL, 0.4 mg/kg, suspended in VEH) over the same period of time. Half an hour after the last dose of haloperidol (PD-56), the rats were placed in photocell monitors and their locomotion activity was assessed for 1 h.

C. Statistical Analysis Of The Data

All results were analyzed by ANOVA followed by post-hoc Scheffe testing where appropriate. Since in the two cohorts tested both at PD-35 and at PD-56 there were no inter-cohort differences for the same lesion status (i.e., ibotenic acid lesioned or sham-operated) in any motor activity measure during any testing interval (i.e., habituation, saline, and amphetamine), the data were combined according to the lesion status. For statistical analysis, vertical activity and total distance traveled were analyzed by ANOVA with STATUS (i.e., SHAM or LESION) as an independent variable, and AGE (i.e., PD-35 or PD-56) and TREATMENT (i.e., habituation, saline, D-amphetamine) as repeated measures. Scheffe test was used for post-hoc comparisons.

The results of the swim test were analyzed by ANOVA with STATUS (i.e., SHAM or LESION) and STRESS (i.e., SWIM or NO STRESS) as independent variables followed by post-hoc tests. The results of haloperidol treatment were also analyzed by ANOVA with STATUS (i.e., SHAM or LESION) and DRUG (i.e., VEH or HAL) as independent variables followed by post-hoc tests.

D. Analysis of the Behavioral Tests

1. Verification of the Lesion

Figure 2:
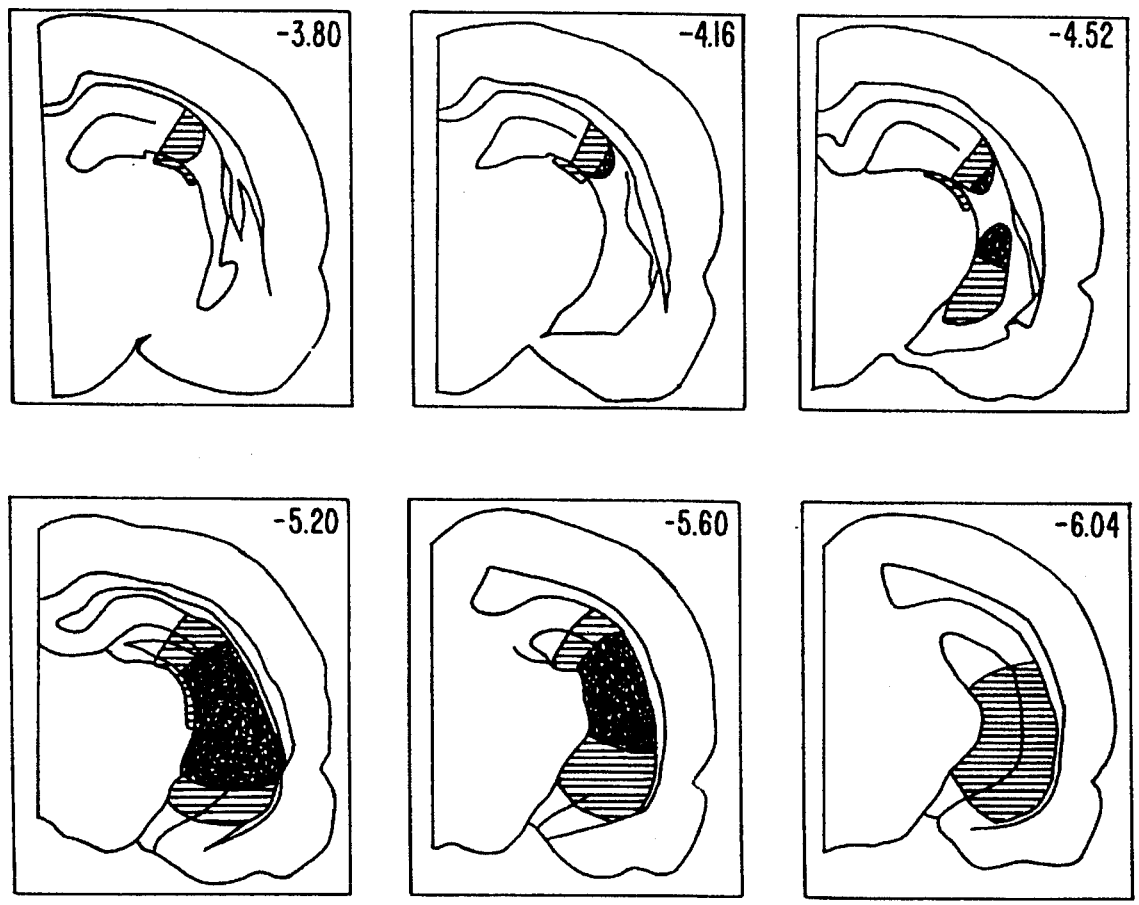
FIG. 2 show lesion boundaries which are defined as the area of neuronal loss and gliosis and determined from Nissl stained coronal sections from 20 rats with ibotenic acid (IA) lesions of the ventral hippocampal formation. Horizontal bars and solid black areas indicate the largest and smallest lesions, respectively. A small rim of injury in the adjacent thalamic region (primary lateral geniculate nucleus) was found in approximately 25% of cases.

Nissl stained sections through the brains of lesioned rats showed sparing of the most anterior (i.e., dorsal) aspects of the hippocampal formation with neuronal loss, atrophy and some cavitation in the ventral hippocampus (FIG. 1.). The dentate gyrus and subiculum were also affected in more posterior (i.e., ventral) parts of the hippocampal formation (FIG. 2.). In most brains, high power investigation of the adjacent regions did not reveal any abnormal glial reaction, loss of neurons, or other obvious pathological changes outside the primary lesion site. However, in a minority of cases (approximately 25%) a small rim of gliosis with minimal neuronal loss could be detected in the thalamic region adjacent to the hippocampus (primarily in the lateral geniculate nucleus). Separate analysis of the behavioral results obtained from these animals did not show any significant differences from those without discernable extra-hippocampal injuries. Therefore, these rats have not been excluded from the study. In a few cases (N=5), histological examination revealed more extensive damage outside the intended lesion site (i.e., neuronal loss and/or cavitation in the septum, cortex, or the thalamus). The results from these animals were excluded.

2. Behavioral Experiments

Exploration, saline injection, D-amphetamine-induced hyperactivity. Analysis of vertical activity showed that during all three testing conditions (i.e., exploration in a novel environment, injection with saline and injection with D-amphetamine), sham and lesioned animals were similar at PD-35. At PD-56, however, the lesioned animals were more active than controls during the exploration period and after amphetamine administration (See, FIG. 3A). ANOVA revealed significant STATUS ($F=4.85$, $P=0.03$), AGE ($F=99.26$, $P<0.001$) and TREATMENT ($F=139.9$, $P<0.001$) effects. There were significant STATUS×TREATMENT ($F=4.60$, $P=0.01$) and AGE ×TREATMENT interactions ($F=90.9$, $P=0.001$). Both STATUS×AGE ($F=3.62$, $P=0.06$) and STATUS×AGE×TREATMENT ($F=2.65$, $P=0.07$) interactions approached significance.

Figure 3:
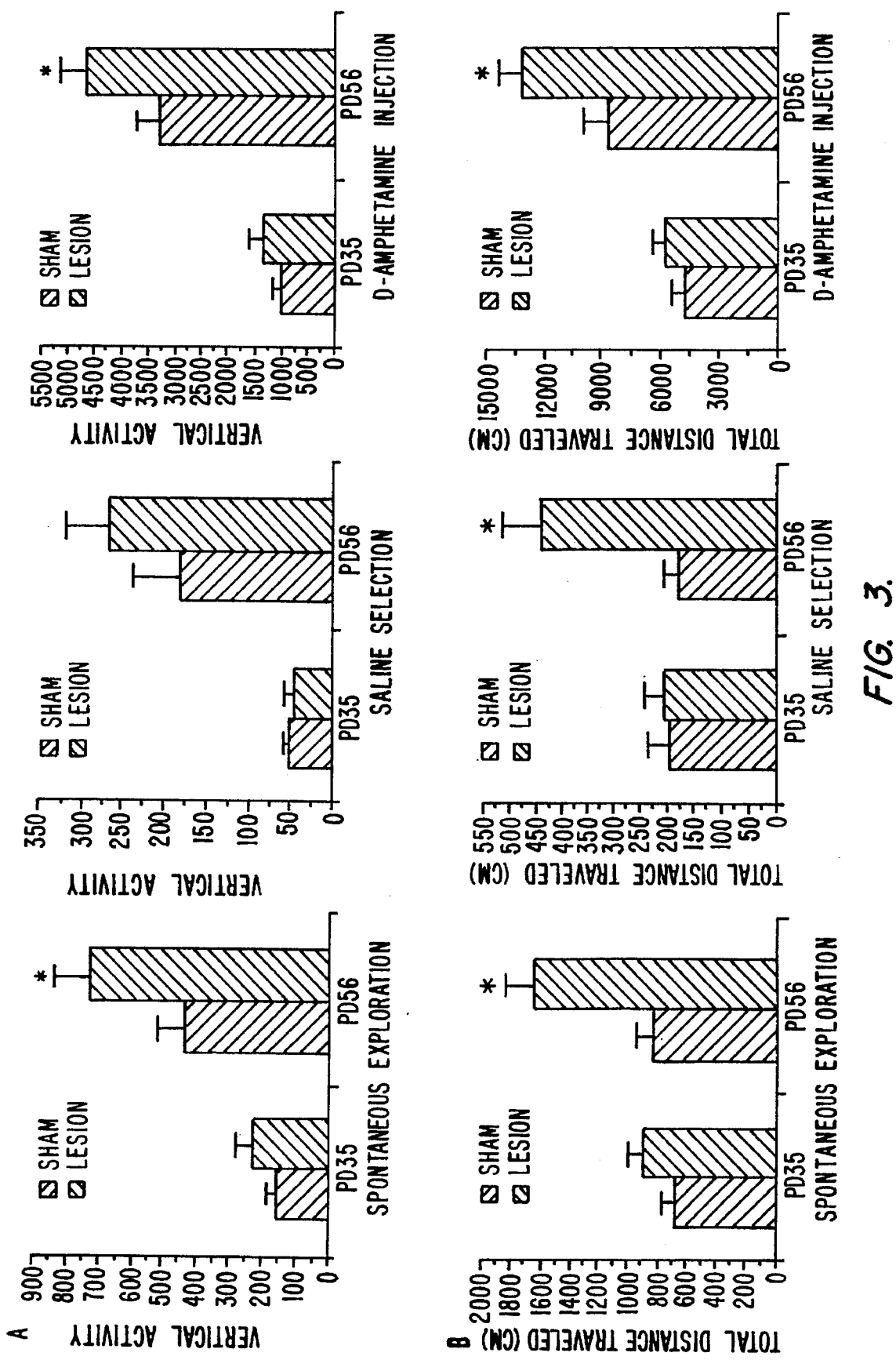
FIG. 3 compares locomotor activity of control (SHAM) and ibotenic acid injected (LESION) groups tested at ages 35 (PD-35) and 56 (PD-56) days. (A) Vertical activity (i.e., the total number of beam interruptions of the vertical sensor) (means±SEM, N=20/group). At PD-35, LESION rats did not differ from SHAM rats at any testing interval. At PD-56, LESION rats were more active than SHAM rats during exploration and after amphetamine (P<0.05). (B) Total distance (cm) traveled (means ±SEM, N=20/group). At PD-35, LESION rats did not differ from SHAM rats at any testing interval. At PD-56, LESION animals were more active than SHAM animals at exploration (P=0.001), after saline (P=0.002), and after amphetamine (P=0.008). LESION rats significantly different from SHAM rats of the same age.

Similarly, total distance traveled by SHAM and LESIONED animals did not differ at PD-35, while at PD-56 lesioned rats were more active than sham operates at all three testing intervals (See, FIG. 3B). ANOVA showed significant STATUS ($F=9.71$, $P=0.004$), AGE ($F=43.44$, $P<0.001$) and TREATMENT ($F=232.8$, $P<0.001$) effects as well as STATUS×TREATMENT ($F=7.40$, $P=0.001$) and AGE×TREATMENT ($F=36.52$, $P<0.001$) interactions. STATUS×AGE ($F=1.64$, $P=0.21$) and STATUS×AGE× TREATMENT ($F=0.45$, $P=0.64$) interactions were not significant.

For the cohort tested at PD-56 only, lesioned animals were hyperactive (11316 ±973 cm, n=18) after D-amphetamine administration compared with SHAM operates (6762±682 cm, n=11, t test, $P=0.002$).

3. Swim Test

Figure 4:
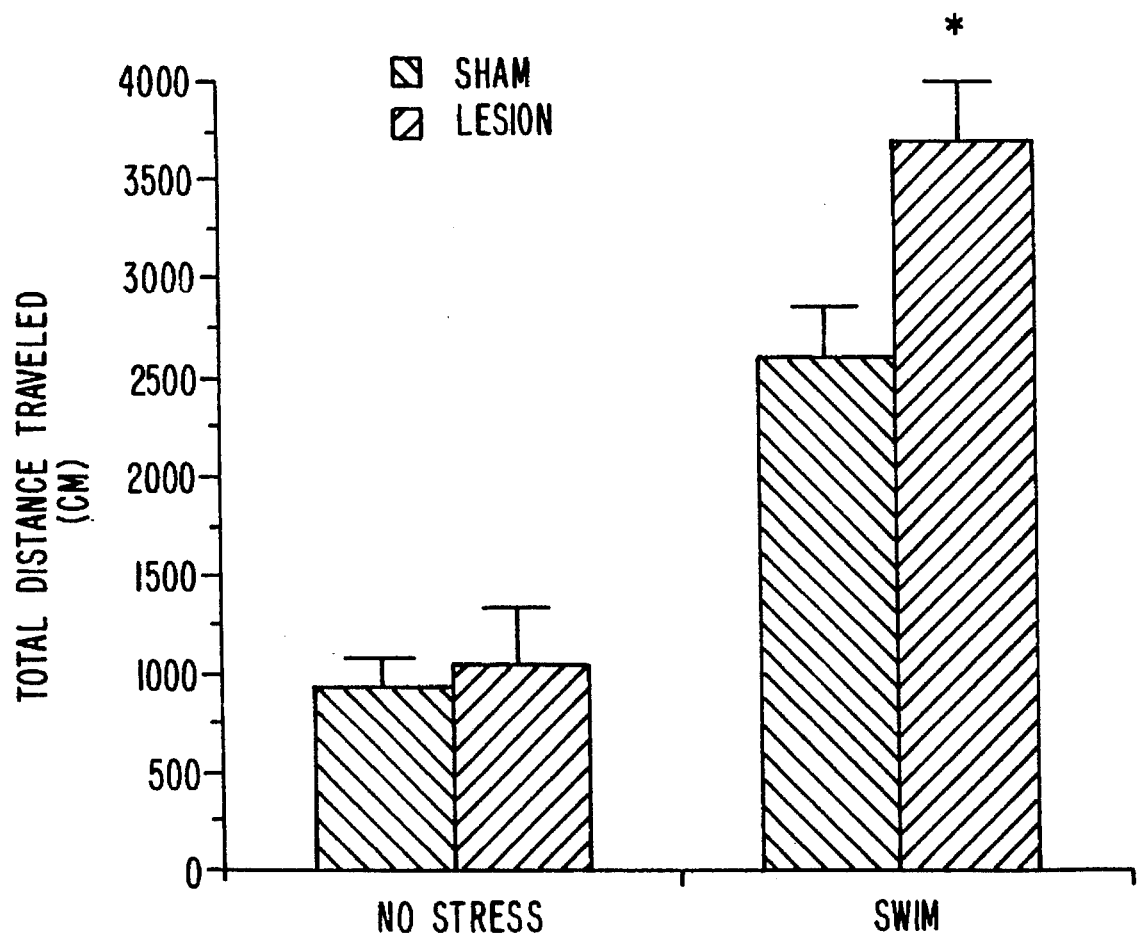
FIG. 4 shows total distance (means±SEM) traveled over 95 min of testing after 15 min swim stress (SWIM) or control exposure (NO STRESS) by rats with SHAM or neonatal ibotenic acid lesions (LESION) of ventral hippocampus (N=8/group). LESION animals significantly different from SHAM animals after exposure to a swim stress (P<0.05).

Moreover, neonatally lesioned animals showed increased activity after exposure to a swim stress at PD-70 (See, FIG. 4). ANOVA revealed significant STATUS ($F=5.55$, $P=0.03$) and STRESS effects ($F=70.65$, $P=0.001$), and marginally significant STATUS×STRESS interaction ($F=3.65$, $P=0.07$). While both SHAM and LESIONED groups were more active in photocell monitors after swimming than after a control exposure (i.e., NO STRESS), the LESIONED rats expressed increased locomotor activity after swim stress in comparison with SHAM/SWIM group ($P<0.05$). Such a stress effect was not seen in a cohort of rats lesioned as adults and tested also at PD-70. In this case, ANOVA revealed a significant STRESS effect ($F=11.62$, $P=0.002$), but no STATUS effect or STATUS×STRESS interaction (n.s.).

4. Haloperidol Treatment

Figure 5:
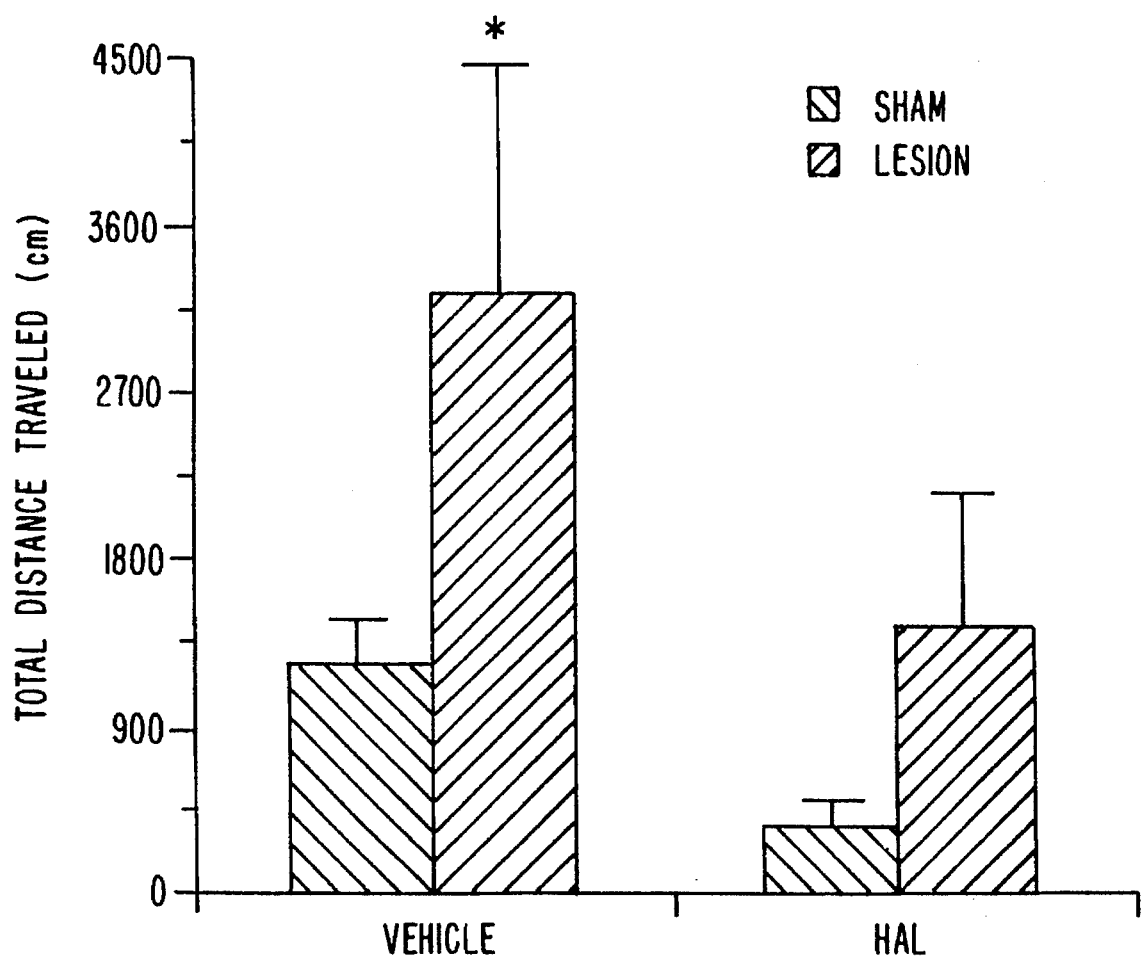
FIG. 5 shows total distance (means±SEM) traveled over 60 min after 3 weeks of vehicle (VEH) or haloperidol (HAL, 0.4 mg/Kg, i.p.) treatment by rats with SHAM or neonatal ibotenic acid lesion of the ventral hippocampus. Untreated lesioned rats are significantly different from all other groups, P<0.05, and their activities are normalized after haloperidol treatment.

Treatment with haloperidol blocked the emergence of hyperactivity in a novel environment at PD-56 in neonatally lesioned animals (See, FIG. 5). ANOVA revealed significant LESION ($F=7.05$, $P=0.01$) and DRUG ($F=5.4$, $P=0.03$) effects, but no LESION×DRUG interaction ($F=1.1$, $P=0.3$). As before, the locomotor activity of the LESION/VEH group was significantly higher than that of the SHAM/VEH group ($P<0.05$). However, the lesioned rats treated with haloperidol were significantly less active than lesioned vehicle-treated rats ($P<0.05$), but not different from SHAM/VEH animals. Haloperidol thus appeared to "normalize" the hyperactivity of the lesioned rats.

The forgoing is offered for purpose of illustration. It will be readily apparent to those skill in the art that the operating conditions, materials, procedural steps and other parameters of the systems described herein may be further modified or substituted in various ways without departing from the spirit and scope of the present invention.

What is claimed is:

1. A rat or mouse artificially brain damaged through a process which introduces a lesion in the ventral hippocampus of the rat or mouse when that rat or mouse is prepubescent, wherein:
   (a) said process comprises injecting a neurotoxin directly into the ventral hippocampus of the prepubescent rat or mouse;
   (b) the neurotoxin causes a lesion by killing the neurons in the ventral hippocampus of said prepubescent rat or mouse; and
   (c) said process results in an artificially brain damaged rat or mouse which, when allowed to reach postpuberty, exhibits abnormal behavior as objectively measured in a standard behavioral test, wherein said abnormal behavior is a behavior which is associated with schizophrenia in humans, and statistically differs from the corresponding behavior of sham lesioned rats or mice.

2. The rat or mouse of claim 1, wherein the neurotoxin is an excitotoxin.

3. The rat or mouse of claim 2, wherein the excitotoxin is selected from the group consisting of ibotenic acid, N-methyl-D-aspartic acid and kainic acid.

4. The rat or mouse of claim 1, wherein the behavioral test measures hyperactivity, locomotor activity, or the response to sensory stimuli.

5. A method of assaying the anti-excessive limbic dopamine activity potential of a pharmaceutical composition, said method comprising:
   (a) administering a pharmaceutical composition thought to have anti-excessive limbic dopamine activity to the postpubescent, artificially brain damaged rat or mouse of claim 1, wherein said rat or mouse exhibits abnormal behavior associated with excessive limbic dopamine activity; and
   (b) objectively measuring the behavior of the rat or mouse of (a) in response to the pharmaceutical composition to determine if there is a decrease in abnormal behavior, wherein said decrease in abnormal behavior is associated with anti-excessive limbic dopamine activity of the pharmaceutical composition.

6. The method of claim 5, wherein the neurotoxin is an excitotoxin.

7. The method of claim 6, wherein the excitotoxin is selected from the group consisting of ibotenic acid, N-methyl-D-aspartic acid and kainic acid.

8. A method of assaying the anti-schizophrenic potential of a pharmaceutical composition, said method comprising:
   (a) administering a pharmaceutical composition thought to have anti-schizophrenic potential to the postpubescent, artificially brain damaged rat or mouse of claim 1, wherein said rat or mouse exhibits abnormal behavior associated with schizophrenia in humans; and
   (b) objectively measuring the behavior of the rat or mouse of (a) in response to the pharmaceutical composition to determine if there is a decrease in abnormal behavior, wherein said decrease in abnormal behavior is associated with anti-schizophrenic potential of the pharmaceutical composition.

9. The method of claim 8, wherein the neurotoxin is an excitotoxin.

10. The method of claim 9, wherein the excitotoxin is selected from the group consisting of ibotenic acid, N-methyl-D-aspartic acid and kainic acid.

11. The method of claim 8, wherein the behavioral test measures hyperactivity, locomotor activity, or the response to sensory stimuli.

* * * * *